United States Patent
Kleinbaum (10) Patent No.: US 9,547,750 B2
(45) Date of Patent: Jan. 17, 2017

(54) SYSTEM AND METHOD FOR PROPAGATING INFORMATION USING MODIFIED NUCLEIC ACIDS

(71) Applicant: Emerald Therapeutics, Inc., Menlo Park, CA (US)

(72) Inventor: Daniel J. Kleinbaum, Yardley, PA (US)

(73) Assignee: Emerald Therapeutics, Inc., South San Francisco, CA (US)

(*) Notice: Subject to any disclaimer, the term of this patent is extended or adjusted under 35 U.S.C. 154(b) by 290 days.

(21) Appl. No.: 14/142,531

(22) Filed: Dec. 27, 2013

(65) Prior Publication Data

US 2014/0114585 A1    Apr. 24, 2014

Related U.S. Application Data

(62) Division of application No. 13/072,438, filed on Mar. 25, 2011, now Pat. No. 8,630,809.

(60) Provisional application No. 61/349,012, filed on May 27, 2010.

(51) Int. Cl.
| | |
|---|---|
| *G06N 3/00* | (2006.01) |
| *G06F 19/22* | (2011.01) |
| *G06N 3/12* | (2006.01) |
| *B82Y 10/00* | (2011.01) |

(52) U.S. Cl.
CPC .............. *G06F 19/22* (2013.01); *B82Y 10/00* (2013.01); *G06N 3/002* (2013.01); *G06N 3/123* (2013.01)

(58) Field of Classification Search
None
See application file for complete search history.

(56) References Cited

U.S. PATENT DOCUMENTS

| | | |
|---|---|---|
| 6,238,927 B1 | 5/2001 | Abrams et al. |
| 6,448,387 B1 | 9/2002 | Slater et al. |
| 7,501,253 B2 | 3/2009 | Pourmand et al. |
| 7,538,202 B2 | 5/2009 | Zhang et al. |

(Continued)

FOREIGN PATENT DOCUMENTS

| | | |
|---|---|---|
| RU | 2124523 C1 | 10/1999 |
| WO | WO-2008/097929 A2 | 8/2008 |

OTHER PUBLICATIONS

Hyrup, B., Egholm, M., Buchardt, O. & Nielsen, P. E. A flexible and positively charged PNA analogue with an ethylene-linker to the nucleobase: Synthesis and hybridization properties. Bioorganic and Medicinal Chemistry Letters 6, 1083-1088 (1996).*

(Continued)

*Primary Examiner* — Soren Harward
(74) *Attorney, Agent, or Firm* — Sheppard Mullin Richter & Hampton LLP (57) ABSTRACT

Improvement is effected for a nucleic acid-based molecular computing system that is comprised of (i) a nucleic acid structure, (ii) at least one polynucleotide displacement molecule that can bind with the nucleic acid structure under hybridizing conditions, and (iii) a clashing polynucleotide molecule that competes with the polynucleotide displacement molecule for binding the nucleic acid structure under the hybridizing conditions. The method for such improvement entails incorporating chemical modification that inhibits the binding of the clashing molecule and the nucleic acid structure or facilitating the binding of the displacement molecule and the nucleic structure.

9 Claims, 9 Drawing Sheets

(56) References Cited

U.S. PATENT DOCUMENTS

| | | |
|---|---|---|
| 2002/0119458 A1 | 8/2002 | Suyama et al. |
| 2003/0152924 A1 | 8/2003 | Ullman et al. |
| 2005/0075792 A1 | 4/2005 | Shapiro et al. |
| 2005/0112614 A1 | 5/2005 | Cook et al. |
| 2007/0072215 A1 | 3/2007 | Seelig et al. |
| 2009/0011956 A1 | 1/2009 | Yin et al. |
| 2009/0170719 A1 | 7/2009 | Kazakov et al. |
| 2009/0191546 A1 | 7/2009 | Zhang et al. |
| 2012/0100633 A1 | 4/2012 | Manetto et al. |

OTHER PUBLICATIONS

Rajeev, K. G., Maier, M. A., Lesnik, E. A. & Manoharan, M. High-Affinity Peptide Nucleic Acid Oligomers Containing Tricyclic Cytosine Analogues. Organic Letters 4, 4395-4398 (2002).*

Wenska, et al., "An activated triple bond linker enables 'click' attachment of peptides to oligonucleotides on solid support," (2011), 39(20):9047-9059.

Biswas et al., "Branch Migration Through DNA Sequence Heterology," *J. Mol. Biol.* (1998) 279:795-806.

Braasch et al., "Locked nucleic acid (LNA): fine-tuning the recognition of DNA and RNA," *Chem. Biol.* (2001) 8:1-7.

Doktycz, in "Nucleic Acids: Thermal Stability and Denaturation," in: eLS. John Wiley & Sons Ltd, Chichester. http://www.els.net [doi: 10.1038/npg.els.0003123] (Oct. 2002).

Dragulescu-Andrasi et al., "Cell-permeable GPNA with appropriate backbone stereochemistry and spacing binds sequence-specifically to RNA," *Chemical Communications* (2005) 2:244-246.

Dragulescu-Andrasi et al., "A Simple (-Backbone Modification Preorganized Peptide Nucleic Acid into a Helical Structure," *J. Am. Chem. Soc.* (2006) 128:10258-10267.

Freier et al., "The ups and downs of nucleic acid duplex stability: structure-stability studies on chemically-modified DNA:RNA duplexes," *Nucleic Acids Research* (1997) 25(22):4429-4443.

Frezza et al., "Modular Multi-Level Circuits from Immobilized DNA-Based Logic Gates," *J. Am. Chem. Soc.* (2007) 129:14875-14879.

International Search Report mailed Nov. 30, 2011, as received in International Patent Application No. PCT/US2011/029947.

Kahan et al., "Towards molecular computers that operate in a biological environment," *Physica D: Nonlinear Phenomena* (2008) 237(9):1165-1172.

Krane et al., "Time for DNA Disclosure," *Science* (2009) 326:631-1632.

Kutyavin et al., "Oligonucleotides Containing 2-Aminoadenine and 2-Thiothymine Act as Selectively Binding Complementary Agents," *Biochemistry* (1996) 35:11170-11176.

Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," *Nucleic Acids Res.* (1986) 14(22):9081-93.

Latimer et al., "Synthetic repeating sequence DNAs containing phosphorothioates: nuclease sensitivity and triplex formation," *Nucleic Acids Res.* (1989) 17(4):1549-61.

Lee et al., "Chitosan: a novel platform in proton-driven DNA strand rearrangement actuation," *Mol. BioSyst.* (2009) 5:391-396.

Li et al., "A new class of homogeneous nucleic acid probes based on specific displacement hybridization," *Nucleic Acids Research* (2002) 30(2)e5, 9 pgs.

Lusvarghi et al., "Loop and Backbone Modifications of Peptide Nucleic Acid Improve G-Quadruplex Binding Selectivity," *Journal of the American Chemical Society* (2009) 131:18415-24.

Maugh II, "Wolf & Lamb Chemistry, Many useful reactions difficult to perform by conventional means can be carried out easily with polymeric reagents," *Science*, (1982) 217:719-720.

Nielsen et al., "An Introduction to Peptide Nucleic Acid," *Current Issues Molec. Biol.* (1999) 1(2):89-104.

Nishikawa et al., "DNA computation simulator based on abstract bases," *Soft Computing* (2001) 5(1):25-38.

Ortega et al., "Binding Affinities of Oligonucleotides and PNAs Containing Phenoxazine and G-Clamp Cytosine Analogues Are Unusually Sequence Dependent," *Organic Letters* (2009) 9(22):4503-4506.

Panyutin et al., "Formation of a Single Base Mismatch Impedes Spontaneous DNA Branch Migration," *J. Mol. Biol.* (1993) 230:413-424.

Panyutin et al., "The kinetics of spontaneous DNA branch migration," *Proc. Natl. Acad. Sci.*, USA (1994) 91:2021-2025.

Picuri et al., "Universal Translators for Nucleic Acid Diagnosis", *J. Am. Chem. Soc.* (2009) 131:9368-9377.

Sager et al., "Designing Nucleotide Sequences for Computation: A Survey of Constraints," *Lecture Notes in Computer Science* (2006) 3892:275-289.

Sahu et al., "Synthesis of Conformationally Preorganized and Cell Permeable Guanidine-Based (-Peptide Nucleic Acids ((GPNAs))," *J. Org. Chem.* (2009) 74:1509-1516.

Seelig et al., "Enzyme-Free Nucleic Acid Logic Circuits", *Science* (2006) 314:1585-1588.

Summerton et al., "Review Article Morpholino Antisense Oligomers: Design, Preparation, and Properties," *Antisense and Nucleic Acid Drug Development* (1997) 7:187-195.

Tajima et al., "Direct Oxidative Cyanation Based on the Concept of Site Isolation", *J. Am. Chem. Soc.* (2008) 130:10496-10497.

Uhlmann et al., "Synthesis and Properties of PNA/DNA Chimeras," *Angewandte Chemical International Edition in English* (1996) 35(22):2632-2635.

Voelcker et al., "Sequence-Addressable DNA Logic," *SMALL* (2008) 4(4):427-431.

Voit, "Sequential One-Pot Reactions Using the Concept of Site Isolation", *Angewandte Chemical International Edition in English* (2006) 45:4238-4240.

Yashin et al., "Networking Particles over Distance Using Oligonucleotide-Based Devices", *J. Am. Chem. Soc.* (2007) 129:15581-15584.

Zhang et al., "Control of DNA Strand Displacement Kinetics Using Toehold Exchange", *J. Am. Chem. Soc.* (2009) 131:17303-17314.

Zhang et al., "Engineering Entropy-Driven Reactions and Networks Catalyzed by DNA," *Science* (2007) 318:1121-1125.

Zhou et al., "Novel Binding and Efficient Cellular Uptake of Guanidine-Based Peptides Nucleic Acids (GPNA)," *J. Am. Chem. Soc.* (2003) 125:6878-6879.

Tanaka Fumiaki et al., "Design of nucleic acid sequences for DNA computing based on a thermodynamic approach", Nucleic Acids Research, 2005, 33(3): pp. 903-911.

Shortreed M.R. et al., "A thermodynamic approach to designing structure-free combinatorial DNA word sets", Nucleic Acids Research, 2006; 33(15): pp. 4965-4977.

Decision on Grant for Russian Application No.: 2012155205 with English translation dated Jun. 28, 2016; 17 pages.

* cited by examiner

SYSTEM AND METHOD FOR PROPAGATING INFORMATION USING MODIFIED NUCLEIC ACIDS

CROSS-REFERENCE TO RELATED PATENT APPLICATIONS

This application claims priority to U.S. provisional application No. 61/349,012, filed May 27, 2010, the entire contents of which are incorporated herein by reference.

BACKGROUND OF THE INVENTION

Nano-scale computers can potentially be realized using molecules. Such computers may be suited for solving certain computation problems. In particular, computers employing biomolecules can be compatible with biological environments, and can potentially be used for complex disease diagnostics or even treatments.

The ability to translate one nucleic acid sequence into another can be employed to build logic gates and networks with nucleic acids. These gates and networks are driven by two events: hybridization and strand displacement. Both events are generally thermodynamically favorable; that is, they involve a transition from a higher to a lower-energy state. Thus, both events can occur spontaneously in a system.

Hybridization involves free, single-stranded stretches of nucleic acids. Accordingly, a nucleic-acid network may be regulated by the availability of these free strands.

A "sequestering event" allows certain sequences to be available conditionally to the rest of the network. Such events empower the construction of translators, which convert one single-stranded nucleic acid sequence into a different single-stranded nucleic acid sequence. These translators are the foundation on which basic logic operators, such as AND, NOT, OR, NAND, NOR, XOR and XNOR, can be built with nucleic acids. From these and other logic components, larger networks can be constructed that include components such as amplifiers. As a result, these translation events are important for information processing with nucleic acids and molecular computing.

SUMMARY OF THE INVENTION

In accordance with one aspect of the present invention, a method is provided for improving a nucleic acid-based molecular computing system. The method includes: (A) identifying a computing system comprised of (i) a nucleic acid structure that includes an incompletely base-paired duplex domain, (ii) at least one polynucleotide displacement molecule that can bind with the nucleic acid structure under hybridizing conditions, such that the nucleic acid structure undergoes a transition in energy state due to a branch migration reaction involving the duplex domain, and (iii) a clashing polynucleotide molecule that competes with the polynucleotide displacement molecule for binding the nucleic acid structure under the hybridizing conditions but that cannot produce a branch migration reaction involving the duplex domain; then (B) reconfiguring at least one of the displacement molecule and the nucleic acid structure, respectively, to incorporate a chemical modification relative to a first reference molecule that comprises natural nucleosides and has the same sequence content as the displacement molecule or the nucleic acid structure, as the case may be. The aforementioned the modification causes binding of the displacement molecule and the nucleic acid structure to have a hybridization free energy, differing from that of a first reference binding between the displacement molecule or the nucleic acid structure and the first reference molecule, such that the branch migration reaction is facilitated relative to the first reference binding. After or in place of step (B) is a step (C) of reconfiguring at least one of the clashing molecule and the nucleic acid structure, respectively, to incorporate a chemical modification relative to a second reference molecule that comprises natural nucleosides and has the same sequence content as the clashing molecule or the nucleic acid structure, as the case may be. The modification causes binding of the clashing molecule and the nucleic acid structure to have a hybridization free energy, differing from that of a second reference binding between the clashing molecule or the nucleic acid structure and the second reference molecule, such that binding of the clashing molecule is impeded relative to the second reference binding.

The invention also provides, in another of its aspects, a system that includes (A) a nucleic acid structure that comprises an incompletely base-paired duplex domain; (B) at least one polynucleotide displacement molecule to effect binding with the nucleic acid structure under hybridizing conditions, such that the nucleic acid structure undergoes a transition in energy state due to a branch migration reaction involving the duplex domain; and (C) at least one polynucleotide clashing molecule capable of binding with the nucleic acid structure under hybridizing conditions, such that the nucleic acid structure and the clashing molecule are bound and prevent the binding of the polynucleotide displacement molecule. At least one of the displacement molecule and the nucleic acid structure, respectively, has a chemical modification relative to a reference molecule that comprises natural nucleosides and has the same sequence content as the displacement molecule or the nucleic acid structure, as the case may be. The modification causes the binding to have a hybridization free energy, differing from that of a reference binding between the displacement molecule or the nucleic acid structure and a reference molecule, such that the branch migration reaction is facilitated relative to the reference binding. In addition or in the alternative, at least one of the clashing molecule and the nucleic acid structure, respectively, has a chemical modification relative to a reference molecule that comprises natural nucleosides and has the same sequence content as the displacement molecule or the nucleic acid structure, as the case may be. The modification causes the binding to have a hybridization free energy, differing from that of a reference binding between the displacement molecule or the nucleic acid structure and a reference molecule, such that binding of the clashing molecule is impeded relative to the reference binding.

In yet another aspect, a system is provided for propagating information. The system includes a first molecule and a second molecule configured to bind with the first molecule. At least one of the first molecule and the second molecule, respectively, has a chemical modification relative to a reference molecule that has the same sequence content as the first molecule or the second molecule, as the case may be. The modification causes the binding to have a free energy different from that of a reference binding between the reference molecule and the first or second molecule, such that at least one of the following is realized in the system: a probability of a productive binding is raised, or a probability of an unproductive binding is reduced.

DETAILED DESCRIPTION

Various approaches, such as solid-phase sequestering, toe-hold sequestering, and toe-hold exchange, can be used in translating nucleic acid sequences to build logic operators and networks. These three particular approaches, described in greater detail below, are exemplified via geometries that utilize three-way, toe-hold-mediated branch migration reactions. Additional mechanisms are possible for branch migration reactions, however, including but not limited to four-way branch migration, four-way accelerated migration, and multi-strand complex migration.

Thus, while the following embodiments are described using three-way branch migration for illustration purposes, the present invention contemplates DNA logic gates and networks built to utilize other branch migration pathways. Conversely, the embodiments of the invention can be applied to any branch migration reaction.

Solid-phase sequestering uses physically separating the relevant sequences/strands in space, using beads, nanoparticles, or surfaces to do so. This approach employs principles of site isolation, which has been used extensively in the organic chemistry context. In solid-phase sequestered geometries, when these displacement events occur can be controlled by regulating whether the necessary strands are in the solution or in the solid phase of the system.

Figure 1A:
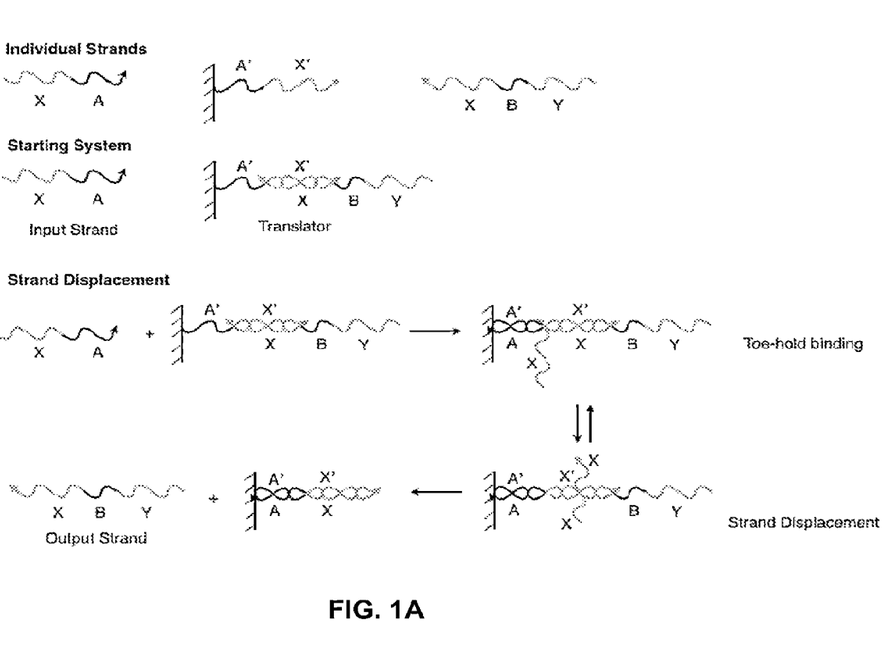
FIG. 1A illustrates a solid-phase sequestering implementation of a nucleic acid translator, where individual section (A, B, etc) represent stretches of oligonucleotides of arbitrary length and sequence.

FIG. 1A shows a basic solid-phase sequestering setup for a translator—a component that allows a system to substitute one nucleic acid sequence for another. Here, the strand A'-X' (where A and X each represent a stretch of oligonucleotides of arbitrary length and sequence and X' and A' represent their respective reverse complements) is bound to a solid support and is initially hybridized to Y-B-X, forming a nucleic acid structure in the form of an incompletely base-paired duplex, which can function as a translator. In this configuration, the strand Y-B-X is solid-phase sequestered and cannot interact with the rest of the system. However, in the presence of the strand X-A, referred to as a "polynucleotide displacement molecule," strand Y-B-X can be displaced from the solid support and exposed to the solution phase of the system, while strand X-A is bound to the support. This operation involves two steps, the first of which is the hybridization of complementary sequences A and A' (often referred to as toe-hold binding). In the second step, the X region of strand X-A binds to the X' region of A'-X', displacing the X region of Y-B-X and releasing this strand into solution while leaving X-A bound to the solid support (this step is often referred to as a branch migration reaction). This two-step process effectively allows for the translation of a free X-A strand into a free Y-B-X strand.

Figure 1B:
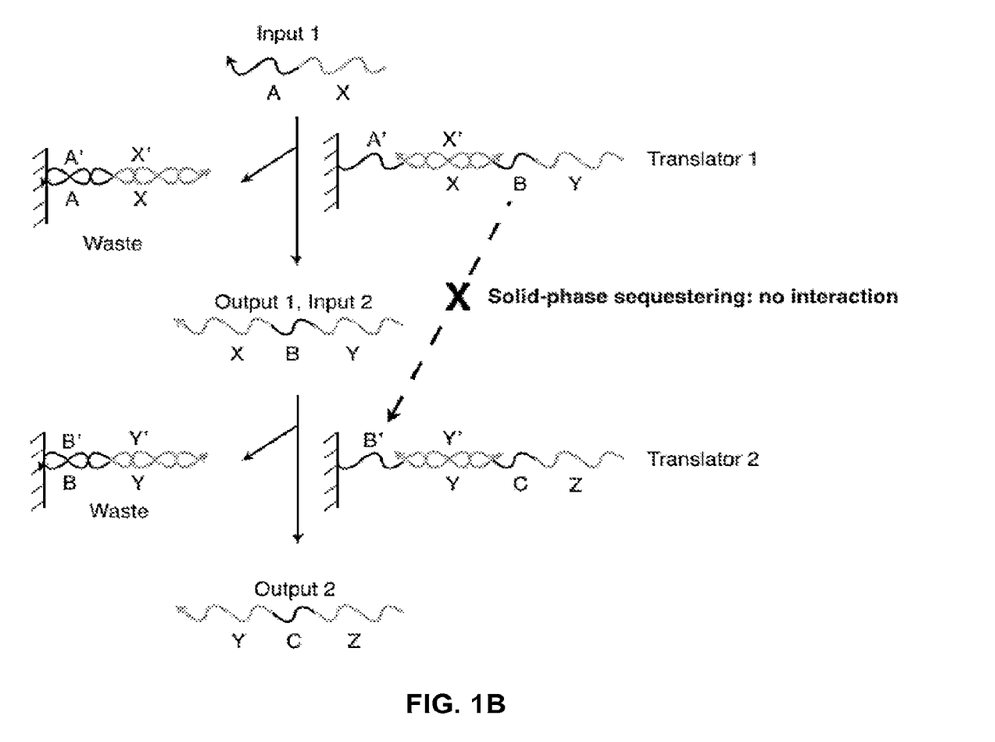
FIG. 1B illustrates how a solid-phase sequestering implementation of a nucleic acid translator sequesters stretches of oligonucleotides.

FIG. 1B shows a system having an input strand X-A interacting with an incompletely base-paired duplex, "Translator 1." The output includes a completely base-paired duplex, A'-X'/X-A, which is considered a "waste" product, and an output strand Y-B-X, which is referred to as "Output 1" and can be used as "Input 2" in a further reaction. "Input 2" interacts with "Translator 2" and produces the "Output 2" and another waste product. In this figure, the B region of strand Y-B-X illustrates the sequestering of sequences in this network. At the start, Y-B-X cannot hybridize with the B' region of Translator 2 because both are isolated on separate solid-supports. When Input 1 binds to Translator 1 and releases Y-B-X into solution, Y-B-X can then interact with Translator 2. Therefore, the ability of Y-B-X and Translator 2 to interact is conditional on the presence of Input 1.

The strands bound to one solid surface interact extremely slowly with strands on another solid surface due to steric effects. Consequently, the strands in the solution phase are the only components that can interact with the solid phase operators.

Toe-hold sequestering and toe-hold exchange are separate approaches that use similar pairing interactions, but with different geometries. Both can accomplish the same operations as solid-phase translators, but function by keeping stretches of sequence bound up in a duplex. Just as in the solid-phase translator, a displacement event can free the sequence of interest. For both toe-hold geometries, all of the strands can be in solution together, by the consequence of which displacement events are regulated by the availability of toe-holds, i.e., short stretches of single-strand nucleic acid sequences that provide a starting point for a displacement event.

Figure 2A:
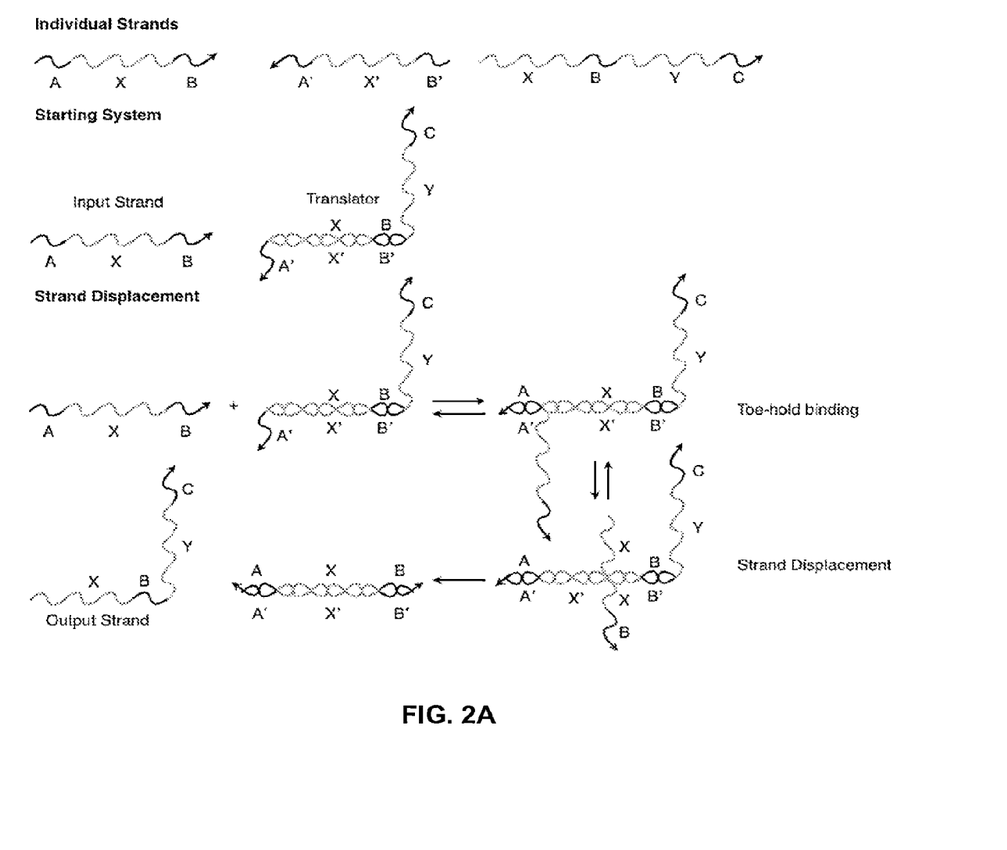
FIG. 2A illustrates a "toe-hold" sequestering implementation of a nucleic acid translator. Again, individual sections represent stretches of oligonucleotides of arbitrary length and sequence.

FIG. 2A shows a toe-hold sequestered translator similar to the one in FIG. 1A, but based on toe-hold rather than solid-phase sequestering. In this example, the A' region of the translator is the toe-hold that binds the input strand and allows the strand displacement reaction to proceed.

Figure 2B:
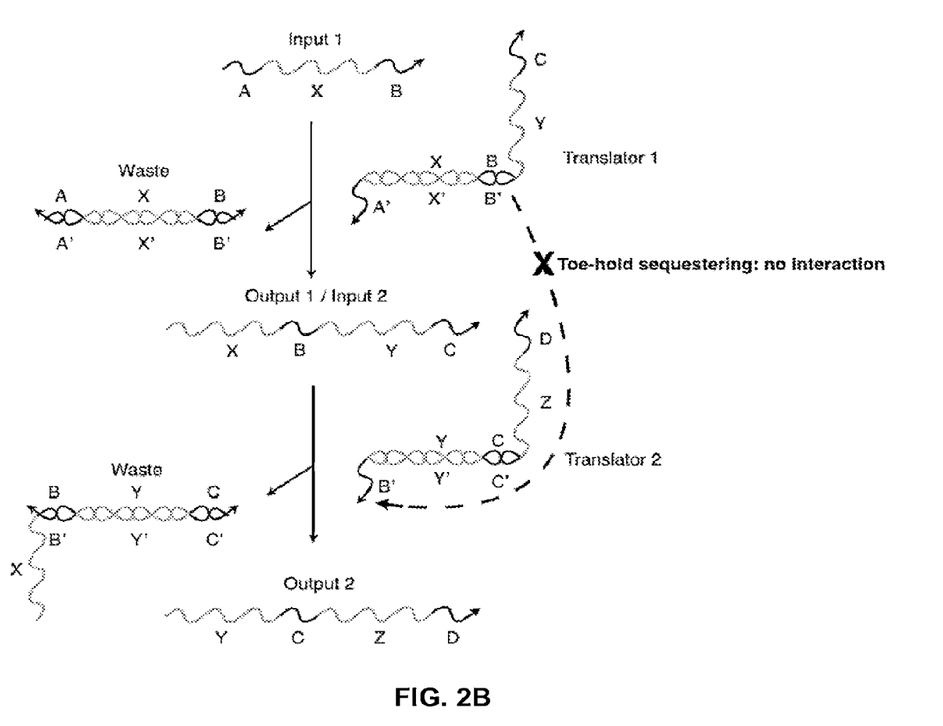
FIG. 2B illustrates how a "toe-hold"-sequestered implementation of a nucleic acid translator sequesters stretches of oligonucleotides.

FIG. 2B shows a toe-hold-based system having an input strand A-X-B interacting with an incompletely base-paired duplex, "Translator 1." The output includes a waste product, i.e., a completely base-paired duplex, B'-X'-A'/A-X-B, and "Output 1" strand X-B-Y-C, which can be used as "Input 2" in a further reaction. "Input 2" interacts with "Translator 2" and produces the "Output 2" and another waste product. In this figure, the B region of X-B-Y-C is sequestered in Translator 1 by being hybridized to a complementary B' region and therefore unable to interact with the B' region of Translator 2. The ability of X-B-Y-C to interact with Translator 2 is conditional on the presence of Input 1 (A-X-B) in the system.

The toe-hold geometries have the potential to be very useful, but their use to date has been limited by the rate at which a system containing such toe-hold geometries can propagate information. This is due to inherent limitations, present in the current toe-hold sequestered approaches, which slow them down below a biologically useful timescale. These kinetic bottlenecks are a result of unproductive reactions, referred to here as "toe-hold clashes," that occur when a toe-hold is bound by a molecule having a complementary sequence or "clashing strand" that cannot produce a displacement reaction.

Figure 3A:
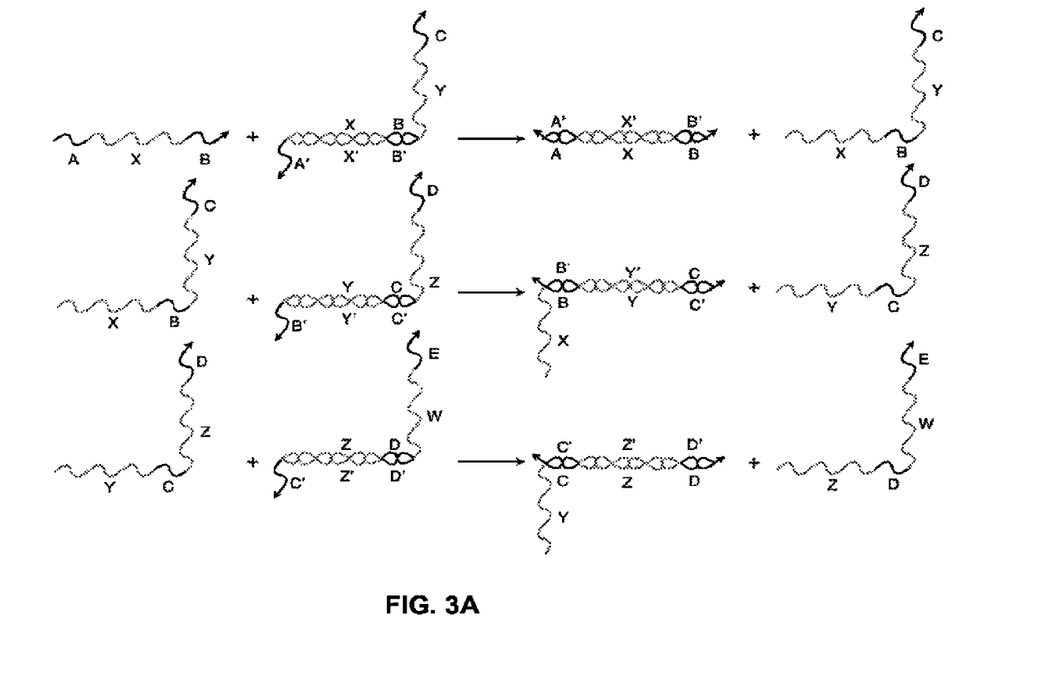
FIG. 3A shows a system of three toe-hold sequestered nucleic acid translators. The reactions shown are all strand-displacement reactions that proceed by the same branch-migration mechanism as in FIG. 2A.
Figure 3B:
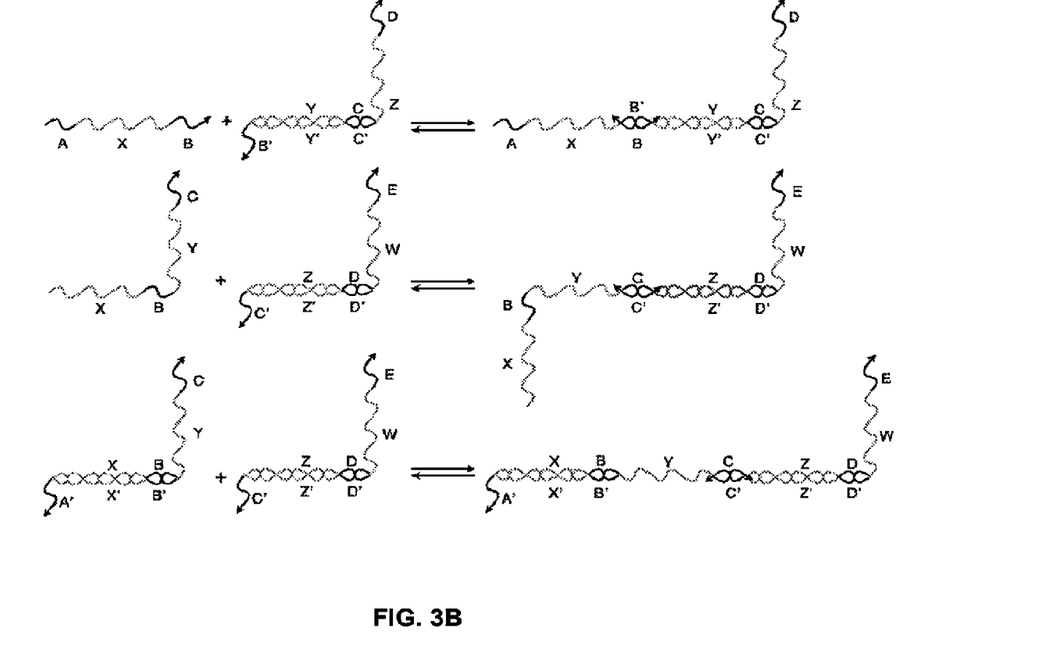
FIG. 3B shows a system with the same oligonucleotides as are shown in FIG. 3A but, instead of strand displacement reactions, toe-hold "clashes" are shown, where the toe-hold is bound by a sequence that cannot produce a strand displacement reaction. This binding event occupies the toe-hold such that the desired strand cannot bind.

FIG. 3A shows a system of three toe-hold sequestered nucleic acid translators, much like the one in FIG. 2A. If all three strands are in solution together, however, there are other binding events that can take place. FIG. 3B illustrates some of the non-productive binding events or clashes that can take place. By involving a "polynucleotide clashing molecule," these events do not lead to a displacement reaction but can slow the system down, because the incidence of a clashing strand blocks strands from binding that can produce a displacement reaction.

Toe-holds can be kept short to mitigate the effect of these clashes on the system: the shorter the toe-hold is, the faster the on/off rate of the complementary sequence can be. Thus, five or six nucleotide-long toe-holds are common because at these lengths, if a non-productive binding event occurs, the time spent in the double-stranded, "clashed" state is short. This approach creates the aforementioned kinetic bottleneck, however, because the productive binding event is constrained by the same thermodynamic parameters; hence, the incoming strand likewise does not bind strongly to these toe-holds. Consequently, the desired displacement does not always occur when the correct incoming strand binds, as it needs to be in the bound state long enough to initiate the displacement reaction. The use of short toe-holds thus increases the amount of time required for a given operation to occur and produce an output. Put another way, the displacement reaction cannot take place before the occurrence of many binding events, both by clashing strands and by desired strands. This inefficiency limits the utility of the system by slowing down the propagation of information to time scales that are too extended to be useful.

Pursuant to one aspect of the invention, by virtue of chemical modification of the nucleic acid structure and/or the polynucleotide displacement molecule, the productive interactions are facilitated. This makes it feasible for chaining individual logic gates together into networks of arbitrary size for biological applications. More specifically, an approach is provided to determine how to disfavor clashing interactions and favor productive interactions without altering the information content of the sequences.

In accordance with the invention, these approaches improve the thermodynamics of binding for the desired strand and/or disfavor the thermodynamics for the clashing strands, all without altering the sequence content. In particular, using chemically-modified structures, the Gibbs free energy ($\Delta G$) for the desired hybridization reaction between a given oligonucleotide and its DNA or RNA complement is reduced and/or the $\Delta G$ of the clashing interaction is increased. On a molecular level, these respectively correspond to a tighter binding (higher binding affinity) of desired hybridization reaction and to a less tight binding (lower binding affinity) for clashing strands, resulting from the modification of the structures.

The former shifts the equilibrium for desired binding events with the toe-hold toward the duplex (bound) state, creating a better chance for the displacement reaction to occur without affecting the equilibrium of binding between the toe-hold and clashing strands. The latter disfavors the binding of the clashing strand(s), making these interactions favor the unbound state. These two changes can be used separately or together, in order to favor the binding of the desired strand and disfavor the binding of the clashing strand(s).

Embodiments in accordance with the invention take advantage of the fact that the reaction rate of any toe-hold mediated strand displacement is related to the thermodynamic favorability of the two nucleic acid strands or complexes being bound. By making these thermodynamics more favorable for the non-clashing binding events and/or less favorable for clashing binding events, one can drive the system toward productive displacement reactions. This will speed up the rate at which information is propagated to the point that it can be used on biologically relevant timescales. The approach of the invention, described here, accomplishes this through chemical modifications to stretches of oligonucleotides in the system.

By virtue of such chemical modification of the nucleic acid structure and/or of the polynucleotide molecule, pursuant to invention, the effective concentration range is widened over which the reaction is optimal. This happens because the percentage of nucleic acid in a duplex at a given temperature is a function of concentration and of the $\Delta G$ of the hybridization reaction. Thus, the more concentrated a set of complementary oligonucleotides is, the higher the percentage of duplex formation and the lower (more favorable) the $\Delta G$ is, the higher the percentage of duplex formation. Changing the $\Delta G$ for a given interaction therefore changes the percent duplex at a given concentration. Lowering the $\Delta G$ (i.e., making the interaction more favorable) means that there will be a higher percentage of duplex at a given concentration, while raising the $\Delta G$ (making the interaction less favorable) means there will be a lower percentage of duplex at the same concentration. This effect widens the optimal concentration range at which these reactions can be practically used, as desired duplexes can be formed at lower concentrations and undesired duplexes will not be formed at higher concentrations, relative to a reference set of unmodified oligonucleotides.

Figure 3C:
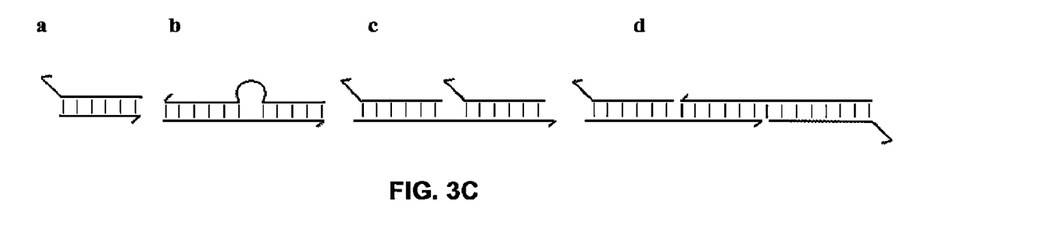
FIG. 3C illustrates different architectures for incompletely base-paired nucleic acid structures including: (a) terminal; (b) internal loop; and (c) and (d) multi-part complex.

These approaches apply to any toe-hold-mediated reaction geometry, including but not limited to the 3-way branch migration reactions discussed above. Different architectures can be used for the incompletely base-paired duplex where branching or loops are located at different points in the structure (see FIG. 3C, for instance). The orientation of the branches or loops is not predicated on the directionality of the strand. Thus, these structures can include (a) a terminal structure, (b) an internal loop, or (c) and (d) a multi-part complex, or any other possible architectures for an incompletely base-paired duplex.

These nucleic acid structures can translate an active "input" sequence (the displacement polynucleotide) into an active "output" sequence (the polynucleotide which is released).

The nucleic acid structures called "translators" above can be at their respective thermodynamic minimum; i.e., they are the most stable structures that the particular set of nucleic acid sequences can form. These structures can be formed by annealing the two or more individual nucleic acid strands. For instance, all of the strands can be mixed together, heated to well above the melting point for any structure to form, and then slowly cooled down. This allows the strands to hybridize in the lowest possible energy state (thermodynamic minimum).

This procedure can be the same for natural nucleic acids like DNA and RNA, nucleic acids with modified backbones, sugars, or bases, and for chimeras made up of natural and modified nucleic acids.

Figure 4:
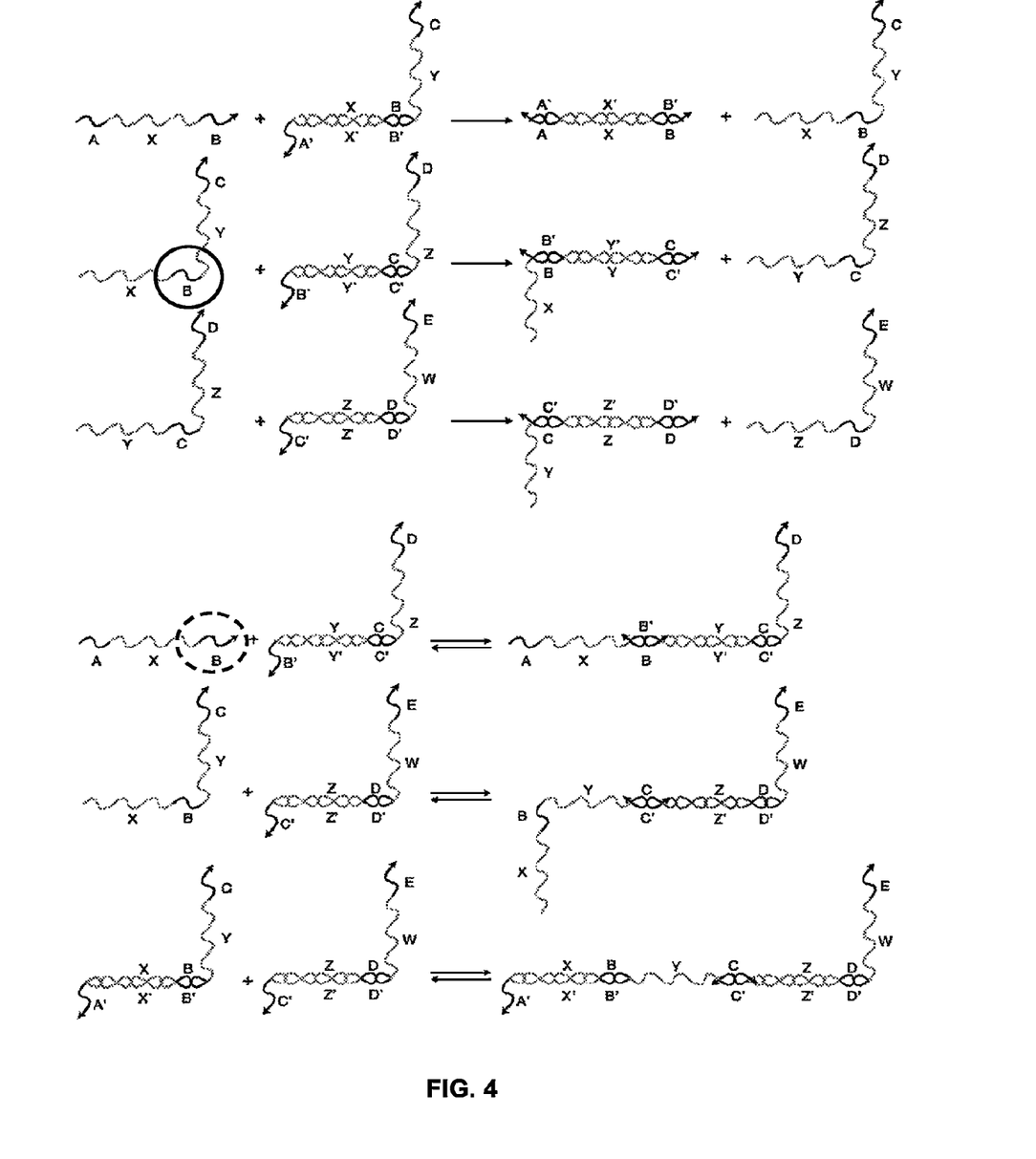
FIG. 4 presents a schematic depiction of how, in the system of nucleic acid translators shown in FIG. 3A, the equilibrium can be shifted to favor strand displacement reactions over toe-hold clashes by replacing the stretches of oligonucleotides with chemical modifications that increase the binding affinity and/or the stretches of oligonucleotides with modifications that decrease the binding affinity.

Selective incorporation of specific chemical modifications can favor the binding of strands capable of productive displacement reactions over toe-hold clash binding events. For example, FIG. 4 shows the same strands as FIGS. 3A and 3B. However, if certain stretches of nucleic acids are replaced with chemically modified analogs that improve the thermodynamics of binding, the kinetics for clashes shifts in favor of the displacement reactions. For example, if the "B" stretch of oligonucleotides in the strand X-B-Y-C (circled with a solid line) has a higher binding affinity for B' than the "B" stretch of oligonucleotides in the strand A-X-B, the equilibrium shifts in favor of the productive, strand displacement reaction, which increases the probability or frequency with which this reaction occurs. Both B's have the same Watson-Crick base pairing sequence, but the interaction between X-B-Y-C and the B' toe-hold is more favorable due to chemical modifications.

Similarly, if certain stretches of nucleic acids are replaced with analogs that disfavor binding, the equilibrium will shift away from the clashes as well. For instance, if "B" in the strand A-X-B (circled with a dashed line) has a lower binding for B' than "B" in X-B-Y-C, then the equilibrium will shift away from the toe-hold clash, improving the kinetics for a strand displacement reaction.

Both approaches accelerate the speed at which a nucleic acid network can process signals because both increase the residence time of the desired strand on the toe-hold relative to the residence time of the clashing strand or strands. This provides a better chance that the strand displacement reaction will occur in a given period of time and thus increases the rate at which the network evaluates a given input or set of inputs. These modifications have not previously been used to facilitate or disfavor displacement reactions, to build significant DNA logic gates and networks, or to propagate information.

There are many well-characterized nucleic acid modifications that can be used in accordance with embodiments of the invention to improve or reduce the thermodynamic properties of binding to natural DNA or RNA. These include changes to the backbone, sugar, or nucleobase of the oligonucleotide. These modifications also can be used separately or in conjunction with one another; that is, using a modified backbone does not preclude the use of a modified nucleobase in the same strand.

Nucleic acid backbone analogs can be used to improve the binding of strands capable of producing a displacement reaction. There are a number of different analogs that could be used, all of which offer tighter binding affinities to DNA and RNA than natural nucleic acids. These analogs include but are not limited to those with uncharged backbones (peptide nucleic acids or phosphorodiamidates), positively charged backbones (guanidinium peptide nucleic acids), and hydrogen-bonding groups that allow for pre-organization (gamma peptide nucleic acids).

Figure 5:
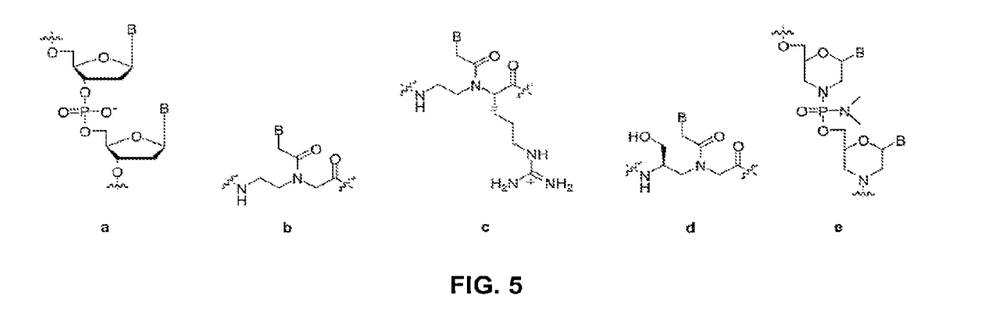
FIG. 5 shows modified backbone structures for nucleic acid analogs, where "B" represents an arbitrary nucelobase, and (a) shows a natural phosphodiester backbone found in DNA, (b) shows peptide nucleic acids, (c) shows guanidinium peptide nucleic acids, (d) shows L-serine derived gamma-PNAs, and (e) shows phosphorodiamidates (here with a morpholino sugar).

The general structures for certain analogs are shown in FIG. 5. These analogs all improve the thermodynamics of nucleic acid hybridization reactions, allowing for tighter toe-hold binding and therefore faster displacement. By using these analogs in specific places of the logic network, the desired displacement reactions can be strongly favored in comparison to the clashing interactions, thus accelerating the rate of information processing.

Figure 6:
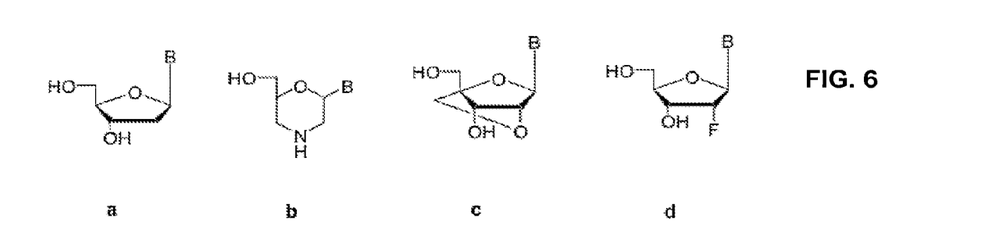
FIG. 6 illustrates modified sugar structures for nucleic acid analogs, where "B" represents an arbitrary nucleobase, and (a) shows a natural deoxyribose sugar found in DNA, (b) shows morpholinos, (c) shows locked nucleic acids, and (d) shows fluorine-modified RNA derivative.

The use of modified sugar rings can also alter the thermodynamics of binding to DNA or RNA for an oligonucleotide. The most widely used analogs are morpholinos, locked nucleic acids (LNAs), and LNA derivatives. Other modified sugars are documented in the literature that also could produce a similar result, in terms of altering binding thermodynamics. Illustrative of these are sugars with modifications at the 1', 2', 3' or 4' position and sugars with different atoms substituted for the oxygen in the ribose cyclopentane ring. These analogs are illustrated in FIG. 6.

Figure 7:
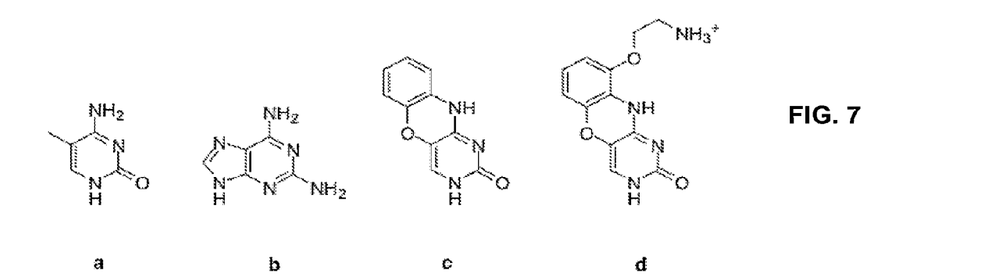
FIG. 7 illustrates modified nucelobase structures for the nucleic acid analogs methylcytosine (a), diaminopurine (b), phenoxazine (c), and G-clamp (d).

Nucleobase modifications can also be used to achieve the same effect as backbone and sugar analogs; namely, altering the thermodynamics of specific hybridization reactions. These bases include methylcytosine, diaminopurine, G-clamp, and phenoxazine (FIG. 7), all of which improve the binding affinity of a strand for its reverse complement. Another opportunity that exists with nucleobase modification involves pseudocomplementary bases. This class of base analogs forms weak base pairs with one another but forms strong base pairs with standard bases. One such pair of bases is 2-aminoadenine (nA) and 2-thiothymine (sT). These bases could be used to favor one strand binding while disfavoring another, an example of increasing the likelihood of a productive binding event while decreasing the likelihood of a clash at the same time.

Another chemical modification that could be used to alter the thermodynamics of binding interactions is the incorporation of charged polymers like chitosan, which has been shown in the literature to accelerate the rate of displacement reactions. However, since these polymers speed up reactions non-specifically, they would have to be used in conjugation with one of the other modifications mentioned above to allow for discrimination between desired and undesired binding events.

Different approaches can be used to synthesize the molecules with the chemical modifications discussed above. For example, the backbone chemistry can be taken into consideration of the design of the modified molecules. Backbone chemistry is what is used to put together individual monomers into a longer strand. Modifications that involve the nucleobase or the sugar but that keep the natural phosphodiester backbone of DNA/RNA can be synthesized via standard phosphoramidite chemistry, as employed for natural monomers. Illustrations of these methods are found, for example, in Beaucage, S., and R. Iyer, *Tetrahedron* 48: 2223 (1992), in Brown, D. M. A, "Brief history of oligonucleotide synthesis," 20 METHODS IN MOLECULAR BIOLOGY (Protocols for Oligonucleotides and Analogs) 1-17 (1993), in Reese, Colin B., *Organic & Biomolecular Chemistry* 3: 3851 (2005), and in Iyer, R. P.; and S. L. Beaucage, "7.05. Oligonucleotide synthesis," 7 COMPREHENSIVE NATURAL PRODUCTS CHEMISTRY (DNA and Aspects of Molecular Biology) 105-52 (1999), the respective contents of which are hereby incorporated by reference in their entirety.

If the backbone is being changed in a particular modification, different chemistry will be employed. Such modification chemistry is generally known in the scientific literature. Thus, peptide nucleic acids (PNAs) and their derivatives rely on amide bonds to link the individual monomers together. Instead of using phosphoramidite chemistry, therefore, strands of these monomers are made with amide bonding forming conditions and coupling reagents like HBTU. An exploration of the methods used to make PNA or PNA-like oligonucleotides can be found, for instance, in F. Beck, "Solid Phase Synthesis of PNA Oligomers," METHODS IN MOLECULAR BIOLOGY SERIES (Peptide Nucleic Acids), Humana Press, http://www.springerlink.com/content/mr571738x7t65067/.

Another backbone modification approach involves chimeric oligonucleotides. These are oligonucleotide strands that contain different backbone chemistries in the same molecule. For example, if one needed a strand that was half PNA backbone and half DNA backbone, one would need a way to join these two different backbone chemistries. Making these chimeric strands is also generally known in the art. In the above example of a PNA/DNA chimera, the difference in chemistries can be bridged by using modified DNA or PNA monomers. For DNA, the 5'-dimethoxytrityl (DMT) protected hydroxyl is replaced with a monomethoxytrityl (MMT)-protected amine that can react with the carboxylic acid of a PNA after deprotection. For PNA, the protected N-terminal nitrogen is replaced with a DMT-protected hydroxyl that can react with the phosphoramidite group on DNA after dc-protection. These approaches are more described in E. Uhlmann, et al., *Angew. Chem.* (Int'l ed.) 37: 2796-823 (1998), for example.

All of these modifications, whether used individually or in conjunction with one another, can affect the thermodynamic conditions of specific interactions in an arbitrary nucleic acid network such that the binding of desired strands or complexes is favored over clashing interactions without altering sequence content. All of these interactions can apply to any branch-mediated migration reaction, whether they are 3-way branch migrations, such as solid-phase sequestering, toe-hold sequestering, or toe-hold exchange, or are branch migrations that take place by other mechanisms, e.g., four-way branch migration, four-way accelerated branch migration, or multi-strand complex migration.

Figure 8:
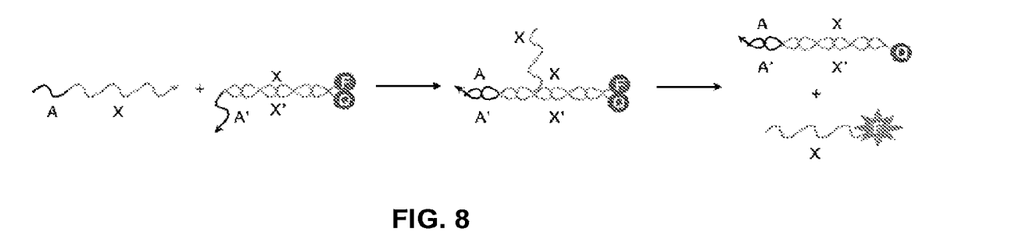
FIG. 8 illustrates a fluorescence kinetics assay for indicating the reaction rate change due to a chemical modification according to the invention.

In accordance with some embodiments, the kinetics of the chemically modified molecules for improved branch migration reaction can be tested. One approach is to measure the improvement that different modifications provide in accelerating or retarding the branch migration reaction versus a natural polynucleotide using a fluorescence kinetics assay (see FIG. 8, for example). Here, the translator structure has a quencher on one strand and a fluorophore on the other. In the absence of the displacement strand, the fluorescence of the fluorophore is quenched, providing a baseline for the reaction. When the displacement molecule, which could be modified in the toe-hold and/or non-toe-hold regions, is added to the translator, it will displace the strand with the quencher and in doing so produce a fluorescent signal. Therefore, the rate of fluorescence "turn-on" in the system indicates the kinetics of the displacement reaction. This assay can be made more complex by requiring a larger circuit to evaluate before a final, fluorescence-producing displacement reaction or clashing strands could be added to compete with the displacement strand for the toe-hold.

The approaches in accordance with the invention also can apply to any molecules, natural or artificial, that are suitable for propagating information, so long as a first molecule and a second molecule are involved, with the latter configured to bind with the former. At least one of the first and second molecules, respectively, has a chemical modification relative to a reference molecule that has the same sequence content as the first molecule or the second molecule, as the case may be. The modification causes the binding to have a free energy different from that of a reference binding between the reference molecule and the first or second molecule, such that at least one of the following is realized in the system: a probability of a productive binding is raised; or a probability of an unproductive binding is reduced.

Pursuant to the invention, as indicated above, a multistep process could be employed to achieve an improved nucleic acid network. This would entail examining the full network of nucleic acid translators under consideration, including any clashing interactions, and then identifying the stretches of sequence that need to be modified in order best to facilitate displacement events and to minimize clashing.

With respect to any given strand displacement reaction, these modifications could be made on the desired displacement molecule, on the clashing molecule, or on both. This is so because, for any translator or logic gate with an available toe-hold, there will be a competition between the desired displacement molecule and any clashing molecule to bind the toe-hold. Furthermore, increasing the ability of the displacement molecule to bind the toe-hold relative to the clashing molecule will increase the rate at which the displacement reaction takes place. Thus, increasing the ability of the displacement molecule to bind (lowering $\Delta G$ of binding) or decreasing the ability of the clashing molecule(s) to bind (raising $\Delta G$ of binding) will have the effect of increasing the rate of the reaction. Since both of these changes in $\Delta G$ can be accomplished via chemical modifications, pursuant to the invention, it is important when considering which stretches of sequence to modify that one should explore the possibility of modifying the displacement molecule alone, the clashing molecule alone, and both of these together.

According to embodiments of the invention, two parameters that could be varied in this analysis are (i) the rate constants for the interaction between any two oligonucleotides and (ii) the length of the toe-holds for all of the oligonucleotides in the network. The former parameter would be dictated by the chemical composition of the oligonucleotide and the $\Delta G$ of its interactions with other oligonucleotides. The latter parameter would be the number of nucleotides in the toe-hold region of sequence under consideration.

The kinetic rate constants needed to model a nucleic acid network could be calculated from the $\Delta G$ of hybridization between any two oligonucleotides. For the natural bases and many of the modifications, these values, which come from nearest-neighbor parameters, have been reported in the literature. If they are not known already, they can be experimentally determined through Van't Hoff analysis of melting temperature data, differential scanning calorimetry, or isothermal titration calorimetry. Each of these methods would yield the thermodynamic parameters for the nucleic acid interaction in question, which then can be used to determine the ΔG of the reaction at any temperature. The ΔG value then would be used to determine the equilibrium constant ($K_{eq}$) of the interaction. The equilibrium constant would be proportional to the ratio of rate constants; hence, one could use known constants to solve for the necessary kinetic rate constant for a given reaction.

Thus, the full set of rate constants would be obtained for the modifications under consideration for use in a nucleic acid logic network, along with the lengths for all of the toe-holds. With this information the system could be modeled to determine the time course behavior of the network, and also to determine where specific modifications could be employed to optimize the productive displacement reactions relative to clashing interactions. Additionally, the length of specific toe-hold regions could be varied in the model. The network would be optimized by varying modifications at specific locations and by simulating the reactions in the network with different length toe-holds. These calculations would be employed to determine the optimal modification and toe-hold length for each component that produces the most favorable time course behavior of the network.

The network also could be optimized by experimentally changing the modifications and toe-hold lengths and then studying the time course behavior in the laboratory, as opposed to simulating the behavior with a mathematical model.

Given a fully optimized network, the necessary oligonucleotides could be synthesized with standard phosphoramidite chemistry or with the approach(es) reported in the literature for specific modifications. Any translator or gate structure that consists of more than one oligonucleotide could be constructed by mixing the individual oligonucleotides together and then annealing them, first by heating the mixture to above the melting temperature of all possible duplexes and then slowly cooling it. This would cause the oligonucleotides to hybridize, forming the most stable structure that the particular set of nucleic acid sequences can adopt. These structures then could be purified before they were used in the network. Once all of the translators, gates, and other components are designed, synthesized, and annealed, the network could be applied to the target assay, diagnostic, or biological system.

While particular embodiments of the subject invention have been discussed, they are illustrative only and not restrictive of the invention. A review of this specification will make many variations of the invention apparent to those skilled in the field of the invention. The full scope of the invention should be determined by reference both to the claims below, along with their full range of equivalents, and to the specification, with such variations.

CITED PUBLICATIONS

The following publications may aid understanding or practicing embodiments of the invention. Each cited publication is incorporated by reference in its entirety.

(1) Picuri, J. M.; Frezza, B. M.; Ghadiri, M. R. *J Am Chem Soc* 2009, 131, 9368-77.
(2) Li, Q.; Luan, G.; Guo, Q.; Liang, *J. Nucleic Acids Res* 2002, 30, E5.
(3) Zhang, D. Y.; Turberfield, A. J.; Yurke, B.; Winfree, E. *Science* 2007, 318, 1121-5.
(4) Frezza, B. M.; Cockroft, S. L.; Ghadiri, M. R. *J Am Chem Soc* 2007, 129, 14875-9.
(5) Voelcker, N. H.; Guckian, K. M.; Saghatelian, A.; Ghadiri, M. R. *Small* 2008, 4, 427-31.
(6) Yashin, R.; Rudchenko, S.; Stojanovic, M. N. *J Am Chem Soc* 2007, 129, 15581-4.
(7) Seelig, G.; Soloveichik, D.; Zhang, D. Y.; Winfree, E. *Science* 2006, 314, 1585-8.
(8) Zhang, D. Y.; Winfree, E. *J Am Chem Soc* 2009, 131, 17303-14.
(9) Biswas, I.; Yamamoto, A.; Hsieh, P. *J Mol Biol* 1998, 279, 795-806.
(10) Panyutin, I. G.; Hsieh, P. *J Mol Biol* 1993, 230, 413-24.
(11) Panyutin, I. G.; Hsieh, P. *Proc Natl Acad Sci USA* 1994, 91, 2021-5.
(12) Maugh, T. H., 2nd *Science* 1982, 217, 719-720.
(13) Tajima, T.; Nakajima, A. *Journal of the American Chemical Society* 2008, 130, 10496-7.
(14) Voit, B. *Angew Chem Int Ed Engl* 2006, 45, 4238-40.
(15) Kahan, M.; Gil, B.; Adar, R.; Shapiro, E. *Physica D-Nonlinear Phenomena* 2008, 237, 1165-1172.
(16) Nielsen, P. E.; Egholm, M. *Curr Issues Mol Biol* 1999, 1, 89-104.
(17) Dragulescu-Andrasi, A.; Zhou, P.; He, G.; Ly, D. H. *Chem Commun (Camb)* 2005, 244-6.
(18) Sahu, B.; Chenna, V.; Lathrop, K. L.; Thomas, S. M.; Zon, G.; Livak, K. J.; Ly, D. H. *J Org Chem* 2009, 74, 1509-16.
(19) Zhou, P.; Wang, M.; Du, L.; Fisher, G. W.; Waggoner, A.; Ly, D. H. *J Am Chem Soc* 2003, 125, 6878-9.
(20) Dragulescu-Andrasi, A.; Rapireddy, S.; Frezza, B. M.; Gayathri, C.; Gil, R. R.; Ly, D. H. *J Am Chem Soc* 2006, 128, 10258-67.
(21) Freier, S. M.; Altmann, K. H. *Nucleic Acids Research* 1997, 25, 4429-4443.
(22) Braasch, D. A.; Corey, D. R. *Chemistry & Biology* 2001, 8, 1-7.
(23) Summerton, J.; Weller, D. *Antisense & Nucleic Acid Drug Development* 1997, 7, 187-195.
(24) Ortega, J. A.; Blas, J. R.; Orozco, M.; Grandas, A.; Pedroso, E.; Robles, *J. Org Lett* 2007, 9, 4503-6.
(25) Kutyavin, I. V.; Rhinehart, R. L.; Lukhtanov, E. A.; Gorn, V. V.; Meyer, R. B., Jr.; Gamper, H. B., Jr. *Biochemistry* 1996, 35, 11170-6.
(26) Lee, D.; Singha, K.; Jang, M. K.; Nah, J. W.; Park, I. K.; Kim, W. J. *Mol Biosyst* 2009, 5, 391-6.
(27) U.S. Pat. No. 7,538,202.
(28) U.S. Patent Application Pub. No. 2005/0112614.
(29) U.S. Patent Application Pub. No. 2007/0072215.
(30) U.S. Patent Application Pub. No. 2009/0191546.

What is claimed is:

1. A nucleic acid-based molecular computing system, comprising:
   (i) an input nucleic acid strand comprising a first fragment (A) and a second fragment (B);
   (ii) a first target, incompletely base-paired nucleic acid duplex comprising a first strand and a second strand, wherein the first strand comprises a first fragment (B') and a second fragment (A'), the second strand comprises a first fragment (B) and a second fragment (C) and the first target duplex comprises a duplex region formed by base-pairing between B and B' and two single-stranded regions, A' and C, and
   wherein A and B of the input strand can bind with A' and B' of the first strand of the first target duplex, respectively, under hybridizing conditions to invoke a strand displacement reaction to produce a first output duplex;
   (iii) a second target, incompletely base-paired nucleic acid duplex comprising a first strand and a second strand, wherein the first strand comprises a first fragment (C')
and a second fragment (B'), the second strand comprises a first fragment (C) and a second fragment (D)
and the second target duplex comprises a duplex
region formed by base-pairing between C and C' and
two single-stranded regions B' and D, wherein B and C of the second strand of the first target
duplex can bind with B' and C' of the first strand of
the second target duplex, respectively, under hybridizing conditions to invoke a strand displacement
reaction to produce a second output duplex, and wherein the second fragment (B) of the input strand can
bind with the single-stranded region B' of the second
target duplex under hybridizing conditions; and (iii) a third target, incompletely base-paired nucleic acid
duplex comprising a first strand and a second strand, wherein the first strand comprises a first fragment (D')
and a second fragment (C'), the second strand comprises a first fragment (D) and a second fragment (E)
and the third target duplex comprises a duplex region
formed by base-pairing between D and D' and two
single-stranded regions C' and E, wherein C and D of the second strand of the second
target duplex can bind with C' and D' of the first
strand of the third target duplex, respectively, under
hybridizing conditions to invoke a strand displacement reaction to produce a third output duplex, and wherein the second fragment (C) of the second strand
of the first target duplex can bind with the single-stranded region C' of the third target duplex under
hybridizing conditions, wherein
the first fragment (B) of the second strand of the first
target duplex comprises a first chemical modification,
relative to a natural nucleic acid, that causes binding
with the second fragment (B') of the first strand of the
second target duplex to have a decreased hybridization
free energy and/or the second fragment (B) of the input strand comprises a
second chemical modification, relative to a natural
nucleic acid, that causes binding with the second fragment (B') of the first strand of the second target duplex
to have an increased hybridization free energy, such that the first fragment (B) of the second strand of the
first target duplex, as compared to the second fragment
(B) of the input strand, binds to the second fragment
(B') of the first strand of the second target duplex to
form a more stable duplex region; and wherein
the first fragment (C) of the second strand of the second
target duplex comprises a third chemical modification,
relative to a natural nucleic acid, that causes binding
with the second fragment (C') of the first strand of the
third target duplex to have a decreased hybridization
free energy and/or the second fragment (C) of the second strand of the first
target duplex comprises a fourth chemical modification, relative to a natural nucleic acid, that causes
binding with the second fragment (C') of the first strand
of the third target duplex to have an increased hybridization free energy, such that the first fragment (C) of the second strand of the
second target duplex, as compared to the second fragment (C) of the second strand of the first target duplex,
binds to the second fragment (C') of the first strand of
the third target duplex to form a more stable duplex
region.

2. The system of claim 1, wherein the input strand, the first target duplex, and the second target duplex form part of an enzyme-free, nucleic acid logic gate selected from the group consisting of an AND gate, a NOT gate, an OR gate, a NAND gate, a NOR gate, an XOR gate, and an XNOR gate.

3. The system of claim 1, wherein the first, the second, the third, or the fourth chemical modification is selected from the group consisting of (i) replacing the sugar-phosphodiester backbone of said nucleosides with a pseudo-peptide backbone, (ii) modifying the sugar moiety of said nucleosides, and (iii) substituting an analogue for the nitrogenous base of at least one of said nucleosides.

4. The system of claim 3, wherein the first, the second, the third, or the fourth chemical modification comprises replacing the sugar-phosphodiester backbone of said nucleosides with a pseudo-peptide backbone into which a guanidinium functional group is incorporated.

5. The system of claim 4, wherein the first, the second, the third, or the fourth chemical modification comprises introducing a heteroatom at the 2'-position of said sugar moiety.

6. The system of claim 4, wherein the first, the second, the third, or the fourth chemical modification comprises substituting a tricyclic cytosine analogue for the nitrogenous base of at least one of said nucleosides.

7. The system of claim 1, wherein the strand displacement reaction comprises a toe-hold-mediated strand displacement.

8. The system of claim 1, wherein the first chemical modification is the same as the third chemical modification.

9. The system of claim 1, wherein the second chemical modification is the same as the fourth chemical modification.

* * * * *

UNITED STATES PATENT AND TRADEMARK OFFICE
CERTIFICATE OF CORRECTION

PATENT NO.        : 9,547,750 B2
APPLICATION NO.   : 14/142531
DATED             : January 17, 2017
INVENTOR(S)       : Daniel J. Kleinbaum It is certified that error appears in the above-identified patent and that said Letters Patent is hereby corrected as shown below:

In the Specification

In Column 1, Lines 63-64, please replace "natural nucleosides" with -- natural nucleotides --.

In Column 2, Lines 9, 34, and 45, please replace "natural nucleosides" with -- natural nucleotides --.

In the Claims

In Claim 3, Column 14, Lines 25-29, please replace:
"replacing the sugar-phosphodiester backbone of said nucleosides with a pseudo-peptide backbone, (ii) modifying the sugar moiety of said nucleosides, and (iii) substituting an analogue for the nitrogenous base of at least one of said nucleosides"

With:
-- replacing the sugar-phosphodiester backbone of nucleotides with a pseudo-peptide backbone, (ii) modifying the sugar moiety of nucleotides, and (iii) substituting an analogue for the nitrogenous base of at least one of nucleotides --.

In Claim 4, Column 14, Line 32, please replace "said nucleosides" with -- said nucleotides --.

In Claim 6, Column 14, Line 42, please replace "said nucleosides" with -- said nucleotides --.

Signed and Sealed this
Ninth Day of May, 2017

Michelle K. Lee
*Director of the United States Patent and Trademark Office*